United States Patent
Ikeda

(10) Patent No.: US 7,042,979 B2
(45) Date of Patent: May 9, 2006

(54) X-RAY DIAGNOSIS APPARATUS HAVING A PLURALITY OF IMAGE ACQUISITION MODES

(75) Inventor: Shigeyuki Ikeda, Kashiwa (JP)

(73) Assignee: Hitachi Medical Corporation, Tokyo (JP)

( * ) Notice: Subject to any disclaimer, the term of this patent is extended or adjusted under 35 U.S.C. 154(b) by 31 days.

(21) Appl. No.: 10/500,321

(22) PCT Filed: Jan. 6, 2003

(86) PCT No.: PCT/JP03/00007

§ 371 (c)(1),
(2), (4) Date: Jun. 28, 2004

(87) PCT Pub. No.: WO03/057039

PCT Pub. Date: Jul. 17, 2003

(65) Prior Publication Data

US 2005/0078793 A1   Apr. 14, 2005

(30) Foreign Application Priority Data

Dec. 28, 2001   (JP) .............................. 2001-399779

(51) Int. Cl.
*H05G 1/64*   (2006.01)
*G01D 18/00*   (2006.01)

(52) U.S. Cl. ................. 378/98.8; 378/98.7; 378/98.11; 378/98.12; 378/207

(58) Field of Classification Search ............... 378/98.8, 378/98.11, 98.12, 98.7
See application file for complete search history.

(56) References Cited

U.S. PATENT DOCUMENTS

| 4,689,487 A | 8/1987 | Nishiki et al. |
| 5,319,206 A | 6/1994 | Lee et al. |
| 5,452,338 A * | 9/1995 | Granfors et al. ......... 378/98.11 |
| 5,920,070 A * | 7/1999 | Petrick et al. ......... 250/370.09 |
| 5,970,115 A * | 10/1999 | Colbeth et al. ............... 378/62 |
| 2002/0064254 A1 | 5/2002 | Aoki et al. |

FOREIGN PATENT DOCUMENTS

| JP | 7-72254 | 3/1995 |
| JP | 07-072254 | 3/1995 |
| JP | 7-236093 | 9/1995 |
| JP | 7-250283 | 9/1995 |
| JP | 2002-204793 | 7/2002 |

OTHER PUBLICATIONS

International Search Report for International Application No. PCT/JP03/00007.

* cited by examiner

*Primary Examiner*—Edward J. Glick
*Assistant Examiner*—Mona Sanei
(74) *Attorney, Agent, or Firm*—Antonelli, Terry, Stout and Kraus, LLP.

(57) ABSTRACT

An offset data calculator has a normal offset data calculation function for calculating offset data based on data obtained from an X-ray flat panel detector while no X-ray is incident in each of the modes, i.e., an entire region fluoroscopy mode, a partial region fluoroscopy mode, imaging mode, etc. and storing the data in an offset data storage device, and additionally has a function for updating, upon calculation of new offset data in any of the modes, another mode offset data stored in the offset data storage device based on the new offset data calculated. Thus, from offset data acquired in any of the plurality of modes, it is possible to obtain the latest offset data in all the modes.

9 Claims, 2 Drawing Sheets

1

X-RAY DIAGNOSIS APPARATUS HAVING A PLURALITY OF IMAGE ACQUISITION MODES

TECHNICAL FIELD

The present invention relates to an X-ray diagnosis apparatus, and in particular, to a method of acquiring offset data for offset-correcting X-ray image data outputted from an X-ray flat panel detector.

BACKGROUND ART

In a conventional technique, an X-ray diagnosis apparatus has a configuration in which a subject is irradiated with an X-ray, and an X-ray image of the subject is displayed on a monitor, etc. based on X-ray image data outputted from an X-ray detector according to the X-ray incident on the X-ray detector after passing through the subject.

The X-ray detector has variations such as an image intensifier and an X-ray flat panel detector. As for the X-ray flat panel detector, an important technology is to eliminate an offset component of a detected element channel which changes over time.

For instance, an indirect X-ray flat panel detector disclosed by U.S. Pat. No. 4,689,487 is comprised of a scintillator (e.g. using cesium iodide (CsI)) for converting an incident X-ray to light and an element for converting the light outputted from the scintillator to electric charge (e.g. a photodiode using amorphous silicon (a-Si)). In addition, a direct X-ray flat panel detector disclosed by U.S. Pat. No. 5,319,206 is comprised of a conversion element using a substance (e.g. selenium (Se) or lead iodide (PbI)) for directly converting the incident X-ray to electric charge.

In either type of X-ray flat panel detector, electric charge outputted from the conversion element constituting each pixel is read out as an image signal through a switching element such as a thint film transistor (TFT). As there is one conversion element per one pixel in the X-ray flat panel detector, it is necessary, in the case where the X-ray flat panel detector has the pixels of 1000 columns×1000 rows, to acquire image data by reading the image signal from a million conversion elements. Thus, to speed up image data acquisition, the pixels are divided into a plurality of pixel groups and readout channels corresponding to the respective pixel groups are provided to perform readout operation in parallel so as to output the image data from each readout channel.

As an offset for each readout channel of the X-ray flat panel detector is different from one another, it is necessary to acquire offset data for each readout channel in advance and use that offset data upon image taking to correct the image data individually for each readout channel.

The X-ray diagnosis apparatus has a radiography mode for reading the image signals individually from all the conversion elements of the X-ray flat panel detector and obtaining a shot image of high resolution (of a large number of pixels), and additionally has a fluoroscopy mode for obtaining a fluoroscopic image of low resolution (of a small number of pixels) at an image rate of 30 images per second for instance. In this fluoroscopy mode, the subject is continuously irradiated with the X-ray and so an X-ray dosage is kept low. Therefore, to improve a signal-to-noise (SN) ratio, the conversion elements are divided into groups (for example, one group is comprised of 2×2 elements) and electric charges obtained from the conversion elements for each group are added up for reading out the image signals.

The offset data are prepared for each of the radiography mode and the fluoroscopy mode so that the offset data used for offset correction is switched according to the mode.

The offset data changes according to a temperature characteristic of a readout circuit, and so it needs to be periodically updated.

As disclosed in Japanese Patent Application Publication No. 7-72254 and Japanese Patent Application Publication No. 2002-204793 (corresponding to U.S. unexamined Patent Publication 2002/0064254 A1), in the case of updating the offset data, a period for not irradiating the X-ray flat panel detector with the X-ray is provided, an arithmetic mean is taken to offset image data of a plurality of frames obtained from the X-ray flat panel detector for each readout channel according to the mode so as to calculate new offset data to be updated.

In an inspection for alternately repeating a plurality of modes such as fluoroscopy and radiography, it is necessary to provide a period without irradiation of X-ray during inspection in order to alternately acquire the offset data. As for a system using the photodiode, there are the cases where an afterimage exists after finishing X-ray irradiation and the offset data cannot be collected until the afterimage is reduced so that the period incapable of X-ray irradiation is extended.

In the case of performing a catheter operation and so on in the fluoroscopic mode, there is the period without X-ray irradiation due to change of a catheter, preparations for a contrast agent and so on so that it is possible to collect the offset data in the fluoroscopy mode in that period. However, there is a problem that it is not possible to secure the period of no X-ray irradiation in the radiography mode and it is difficult to acquire the offset data in the radiography mode because the radiography is performed by shifting from the fluoroscopy mode to the radiography mode immediately (in one to two seconds ordinarily) and it moves from the radiography mode to the fluoroscopy mode immediately after finishing the radiography to check a catheter status.

Furthermore, incident dosage is large enough in the radiography mode to reduce influence on an image caused by variation of an offset less than that in the fluoroscopy mode. In the case where offset data are not acquired for a long time, artifacts may be generated in the image. The change in the offset may significantly influence image quality in the case of adopting the mode for obtaining the fluoroscopic image (partial region fluoroscopy mode) by using the pixels of the radiography mode while keeping the resolution and limiting a field of view without adding pixels.

Moreover, the offset data may be collected by each pixel in place of each readout channel of the X-ray flat panel detector. In this case, there is a problem that collection of the offset data is time-consuming, and in particular, it is more time-consuming in the radiography mode than in the fluoroscopy mode because of a large number of pixels in the radiography image.

The present invention is provided in consideration of such circumstances, and an object thereof is to provide an X-ray diagnosis apparatus capable of acquiring offset data in another mode from the offset data acquired in one of a plurality of modes, and performing a precise offset correction equivalent to newly acquiring offset data in all the modes.

DISCLOSURE OF THE INVENTION

To attain the above object, the present invention relates to an X-ray diagnosis apparatus comprises: an X-ray generator for generating X-ray according to an X-ray generating condition of an image acquisition mode selected from a plurality of image acquisition modes; an X-ray detector for receiving incidence of the X-ray generated by the X-ray generator, the X-ray detector converts the incident X-ray to an image signal and processes the image signal according to a signal processing condition of the selected image acquisition mode to thereby outputs image data in the selected image acquisition mode; storage means for storing each of offset data in the plurality of image acquisition modes; first mode offset data calculation means for, when a first mode of the plurality of image acquisition modes is selected, calculating new offset data in the first mode based on offset image data outputted from the X-ray detector in a state that the X-ray is not incident on the X-ray detector and first mode offset data stored in the storage means; second mode offset data calculation means for calculating new offset data in a second mode based on second mode offset data of the plurality of image acquisition modes stored in the storage means and the new offset data in the first mode; image calculation means for, when the second mode is selected, calculating a second mode X-ray image from the image data outputted from the X-ray detector in a state that the X-ray is incident on the X-ray detector and the new offset data in the second mode; and display means for displaying the X-ray image.

Preferably, the offset data stored in the storage means are acquired in advance in the state that the X-ray is not incident on the X-ray detector.

Preferably, the second mode offset data calculation means calculates the new offset data in the second mode by converting the second mode offset data stored in the storage means based on at least one of an update amount and an update rate of the new offset data in the first mode.

Preferably, the first mode offset data calculation means calculates the offset data in the first mode by obtaining arithmetic means of a plurality of the offset image data in the first mode for each pixel of the offset image data or for each readout channel of the X-ray detector so as to calculate the offset data in the first mode.

Preferably, the X-ray detector is an X-ray flat panel detector.

According to the present invention, if the offset data is newly calculated in one of a plurality of modes for acquiring the X-ray image data, it is possible to update the offset data in another mode stored in offset data storage means based on the offset data.

For instance, the offset data acquired in a fluoroscopy mode is used to calculate variation of the offset data in a radiography mode so as to update the offset data in the radiography mode. Alternatively, the offset data acquired in the radiography mode is used to calculate the variation of the offset data in the fluoroscopy mode so as to update the offset data in the fluoroscopy mode. Alternatively, the offset data are updated as in the above between an entire region fluoroscopy mode for adding pixels and a partial region fluoroscopy mode for adding no pixel. Thus, it is possible to eliminate artifacts from a radiographic image or a fluoroscopic image in a case of repeatedly using the fluoroscopy mode and radiography mode or the entire region fluoroscopic mode and partial region fluoroscopy mode to perform an inspection.

BEST MODE FOR CARRYING OUT THE INVENTION

Hereinafter, a preferred embodiment of an X-ray diagnosis apparatus according to the present invention will be described in detail according to the attached drawings.

Figure 1:
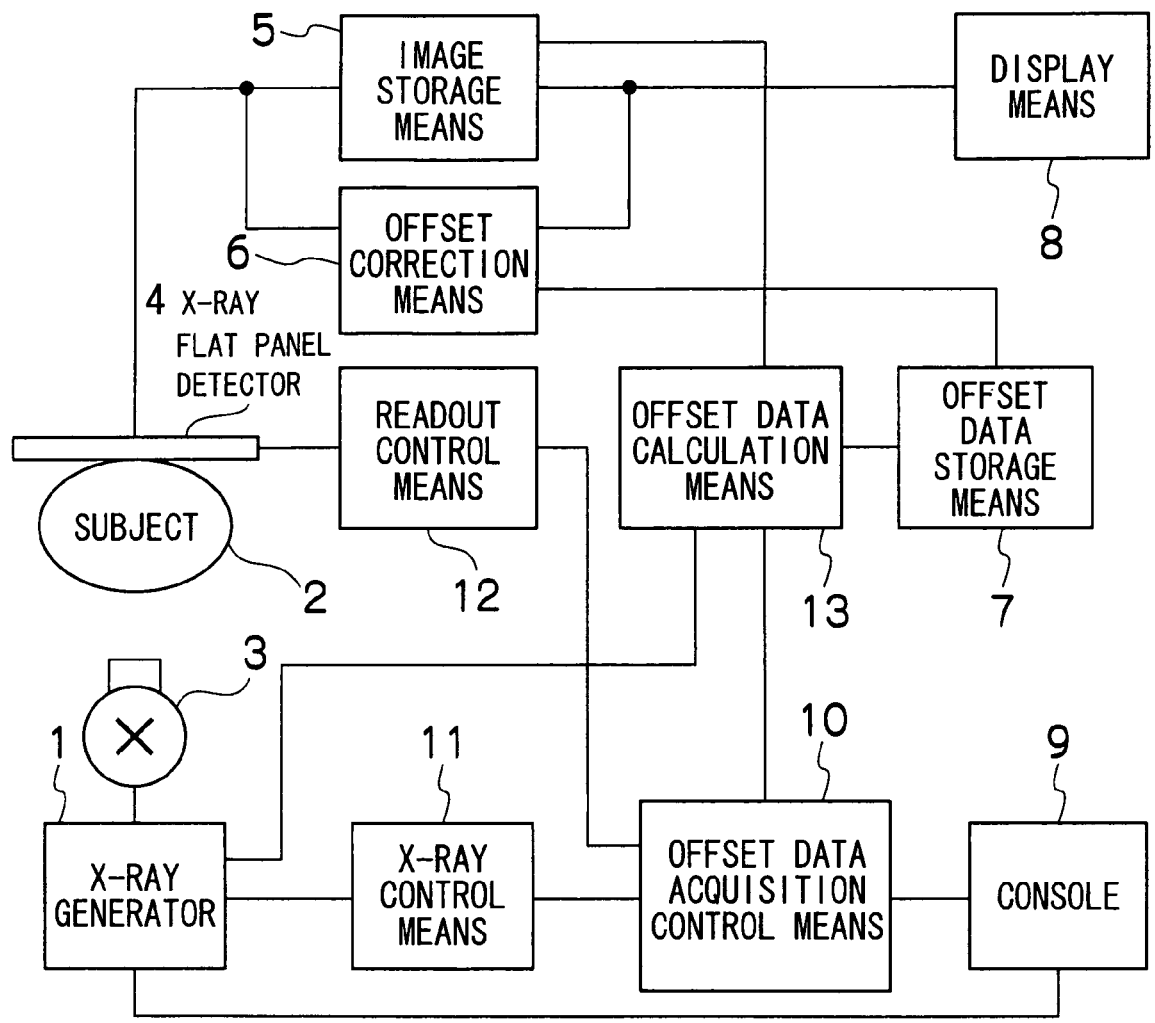
FIG. 1 is a block diagram showing an overview configuration of an embodiment of an X-ray diagnosis apparatus according to the present invention.

FIG. 1 is a block diagram showing a schematic configuration of the X-ray diagnosis apparatus according to the present invention. As shown in FIG. 1, the X-ray diagnosis apparatus according to the present invention includes an X-ray source 3 controlled by an X-ray generator 1 to irradiate a subject 2 with an X-ray, an X-ray flat panel detector 4 placed opposed to the X-ray source 3 for outputting X-ray image data according to the X-ray incident after passing through the subject 2, image storage means 5 for storing the X-ray image data outputted from the X-ray flat panel detector 4 as digital data, offset correction means 6 for performing offset correction to X-ray image data stored by the image storage means 5 and making the image storage means 5 again store X-ray image data after the offset correction stored by the image storage means 5, offset data storing means 7 for storing offset data for performing an offset correction on the X-ray image data with the offset correction means 6, display means 8 for displaying the X-ray image data stored in the image storage means 5 as an image, offset data acquisition control means 10 for controlling offset data acquisition according to an instruction of an operator from a console 9, an X-ray control means 11 for controlling the X-ray generator 1 to irradiate no X-ray from the X-ray source 3 according to an instruction from the offset data acquisition control means 10, readout control means 12 for controlling readout of the X-ray image data from the X-ray flat panel detector 4 according to the instruction from the offset data acquisition control means 10, and offset data calculation means 13 for calculating the offset data of each readout channel of the X-ray flat panel detector 4 from the X-ray image data read from the readout control means 12 and having it store, by the offset data storage means 7.

The offset correction means 6 reduces influence of an offset by subtracting the offset data stored in the offset data storage means 7 from input image data in advance. The offset data stored in the offset data storage means 7 are acquired as the offset data of which noise influence is reduced by reading a plurality of image data when irradiating no X-ray and performing an arithmetic mean process with the offset data calculation means 13.

Next, operation for updating the offset data according to the embodiment of the present invention will be described. The offset data are the offset data of each readout channel of the X-ray flat panel detector 4 or the offset data of each pixel read from the X-ray flat panel detector 4. Hereinafter, a description will be given as to the case of obtaining and updating the offset data of each pixel.

In the case of updating the offset data, an instruction to update the offset data is inputted by a switch and so on of the console 9, wherein X-ray irradiation from the X-ray generator 1 is interlocked and a state that is no X-ray incident on the X-ray flat panel detector 4 is established. In this state, the offset data acquisition control means 10 outputs a command to acquire offset image data for updating the offset data to the readout control means 12 and has the image storage means 5 acquire offset image data for updating the offset data. The offset data calculation means 13 captures the offset image data of a plurality of images via the image storage means 5, and performs the arithmetic mean process to the offset image data for each pixel so as to calculate the offset data. The offset data thus calculated is stored by the offset data storage means 7.

As such offset data are different according to the mode for acquiring the images, the same process is performed in each mode so that the offset data storage means 7 has the offset data for each of the plurality of modes recorded therein. The offset correction means 6 performs the offset correction by selecting corresponding offset data according to the modes from the offset data in the plurality of modes stored in the offset data storage means 5.

Even in the case where the above process is performed, the offset may vary due to temperature rise of the X-ray flat panel detector 4 and so on. Therefore, the above process needs to be periodically repeated as to all the modes.

The X-ray flat panel detector 4 often has the plurality of modes according to purposes of radiography. For instance, a radiography mode for reading electric charges individually from all conversion elements of the X-ray flat panel detector 4 and obtaining a radiographic image of high resolution and an entire region fluoroscopy mode for obtaining a fluoroscopic image of low resolution at an image rate of 30 images per second.

Figure 2:
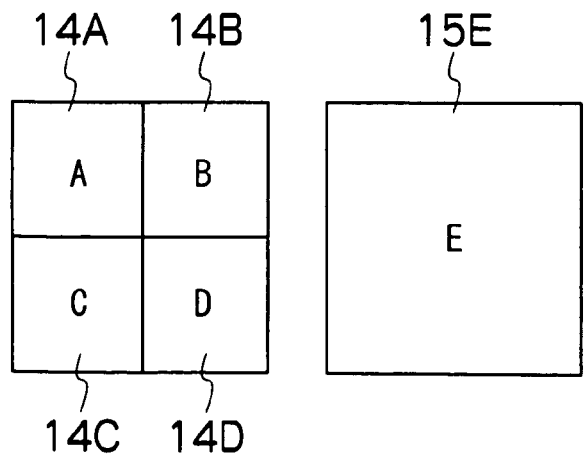
FIG. 2 is a diagram used to describe pixels in a radiography mode and pixels in an entire region fluoroscopy mode.

FIG. 2 shows four pixels 14A, 14B, 14C and 14D in the radiography mode and a pixel 15E in the fluoroscopy (low dosage) mode.

The pixel 15E in the entire region fluoroscopy mode is equivalent to the sum total of the four pixels 14A, 14B, 14C and 14D in the radiography mode (that is, the four pixels (2×2) of the X-ray flat panel detector 4). Therefore, if the four pixels 14A, 14B, 14C and 14D are added and the pixel 15E in the entire region fluoroscopy mode is calculated, sensitivity becomes four times higher than the case of not adding them so that the fluoroscopic image having a good SN ratio can be created from an image of small incident dosage.

When the offset data of the pixels 14A, 14B, 14C and 14D in the radiography mode is a, b, c and d, the offset data e of the pixel 15E can be approximately acquired by adding the offset data a to d as in the following formula (1).

$$e = a + b + c + d \quad (1)$$

Therefore, the offset data in the entire region fluoroscopy mode (addition mode) can be calculated if the offset data in the radiography mode (non-addition mode) is acquired.

In an actual inspection, radiography is performed immediately after inserting a catheter and a guide wire and determining a radiographic position while performing fluoroscopy, and after the radiographic, the fluoroscopy is immediately performed again in order to check a state of the catheter and a guide wire and remove these. Specifically, the inspection is performed in the entire region fluoroscopy mode under normal circumstances, and it moves on to the radiography mode when starting the radiography so as to move on to the entire region fluoroscopy mode immediately after the radiography.

In the entire region fluoroscopy mode, there is a period for temporarily irradiating no X-ray due to replacement of the catheter and so on, and so it is possible to obtain the offset image data for updating the offset data during that period. As the entire region fluoroscopy mode can reduce the number of pieces of readout data by adding the pixels so that it is often possible to secure the image rate of 30 images per second by speeding up the readout of the data. In reality, to curb influence of noise, for example 64 to 128 offset images are obtained, an offset data with its SN ratio improved is calculated by obtaining the arithmetical mean thereof for each pixel of the offset image (or for each readout channel of the X-ray flat panel detector 4). Therefore, in the case of using the data of 128 images as the offset image data, it is possible to obtain all the images in about four seconds at the rate of 30 images per second so that the data can be acquired in the aforementioned period for temporarily irradiating no X-ray. In the radiography mode, however, the number of pixels is four times that of the entire region fluoroscopy mode, and the image rate is reduced to a quarter of that of the entire region fluoroscopy mode and becomes 7.5 images per second. As it requires about 16 seconds to acquire 128 images at this image rate, there is a possibility that the offset image data for updating the offset data in the radiography mode cannot be acquired in the aforementioned period for temporarily irradiating no X-ray.

Because, in the entire region fluoroscopy mode, resolution of the image deteriorates by adding four pixels, a partial region fluoroscopy mode for implementing high-speed capturing without reducing the resolution by adding no pixel and reducing a view size is also used.

Figure 3:
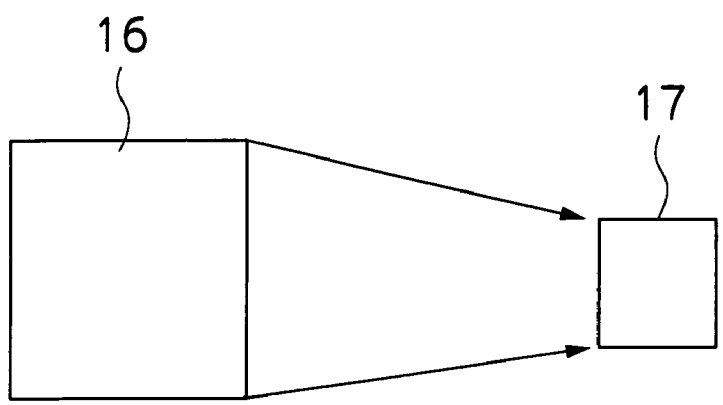
FIG. 3 is a diagram showing an outline of obtaining a fluoroscopic image of a small number of pixels by adding the pixels in the entire region fluoroscopy mode.
Figure 4:
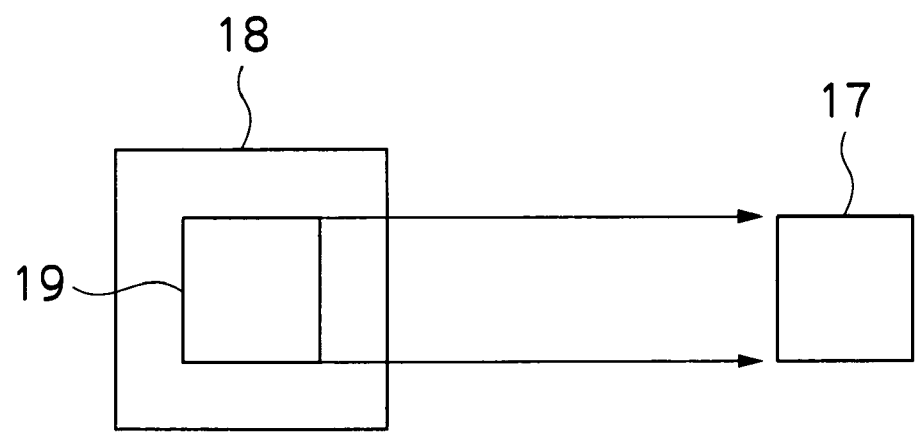
FIG. 4 is a diagram showing an outline of obtaining a fluoroscopic image of a small number of pixels by reducing a field of view size in a partial region fluoroscopy mode.

FIG. 3 is an example of the entire region fluoroscopy mode in which four pixels are added, and an output image 17 is acquired by adding four pixels 16 indicating an effective field of view of the X-ray flat panel detector 4. In this case, it is possible to image all the fields of view, but the resolution deteriorates. FIG. 4 shows the partial region fluoroscopy mode for adding no pixel and reading at high speed, where it reads without adding the pixels only an area 19 which is a quarter of a pixel 18 indicating the effective field of view which can be imaged so as to obtain the output image 17. The areas other than the area 19 which is a quarter of the pixel 18 indicating the effective field of view are devised not to have the subject 2 irradiated with the X-ray by means of a collimator and so on under normal circumstances. And in the case of collecting the images by a fluoroscopy dosage, required luminance is secured by, for example, quadrupling a gain of a readout amplifier. In this case, a configuration for calculating the output pixels is different even in a switch over between the fluoroscopy modes, whereby there is a possibility that artifacts may be generated if the offset data is not updated when the entire region fluoroscopy mode is switched over to the partial region fluoroscopy mode of adding no pixel after continuing the fluoroscopy in the entire region fluoroscopy mode of adding the four pixels.

Next, a description will be given as to the case of updating the offset data in another mode based on the offset data newly calculated in one of the radiography mode, the entire region fluoroscopy mode and the partial region fluoroscopy mode.

"The case where the offset data is newly calculated in the radiography mode"

If the offset data is newly calculated in the radiography mode, the offset data in the entire region fluoroscopy mode can be approximately acquired by adding the offset data of 2×2 as shown in the formula (1). As for the offset data in the partial region fluoroscopy mode, it is possible to adopt the offset data equivalent to a relevant area out of the offset data newly calculated in the radiography mode as-is.

"The case where the offset data is newly calculated in the entire region fluoroscopy mode"

If the offset data is newly calculated in the entire region fluoroscopy mode, the offset data in the radiography mode can be calculated as follows.

When the offset data before updating the pixels 14A, 14B, 14C and 14D in the radiography mode stored in the offset data storage means 7 is $a_1$, $b_1$, $c_1$ and $d_1$, the offset data before updating the pixels 15E in the entire region fluoroscopy mode stored in the offset data storage means 7 is $e_1$, and the offset data newly calculated in the entire region fluoroscopy mode is $e_2$, the new offset data $a_2$, $b_2$, $c_2$ and $d_2$ in the radiography mode is calculated by the following formula (2) or (3).

$$a_2 = a_1 \times e_2/e_1$$
$$b_2 = b_1 \times e_2/e_1$$
$$c_2 = c_1 \times e_2/e_1$$
$$d_2 = d_1 \times e_2/e_1 \quad (2)$$

Or $$a_2 = a_1 + \{(e_2 - e_1)/4\}$$
$$b_2 = b_1 + \{(e_2 - e_1)/4\}$$
$$c_2 = c_1 + \{(e_2 - e_1)/4\}$$
$$d_2 = d_1 + \{(e_2 - e_1)/4\} \quad (3)$$

According to the formula (2), the offset data in the radiography mode stored in the offset data storage means 7 can be converted based on an update rate of the new offset data in the entire region fluoroscopy mode so as to calculate the new offset data in the radiography mode. According to the formula (3), the offset data in the radiography mode stored in the offset data storage means 7 can be converted based on an update amount of the new offset data in the entire region fluoroscopy mode so as to calculate the new offset data in the radiography mode. Furthermore, it is also possible, by weighting and adding results calculated by both the formulas (2) and (3) for instance, to calculate the new offset data in the radiography mode in consideration of both the update amount and update rate of the new offset data in the entire region fluoroscopy mode.

It is possible, by the method, to approximately acquire the offset data in the radiography mode from the offset data acquired by adding the four pixels in the entire region fluoroscopy mode so as to update the offset data in the radiography mode with approximate data before updating the offset data in the radiography mode by an ordinary method in the inspection. Thus, it becomes feasible to eliminate or significantly reduce an artifact of the shot image. The offset data in the partial region fluoroscopy mode of which view size is small can also be updated as above.

"The case where the offset data is newly calculated in the partial region fluoroscopy mode"

Figure 5:
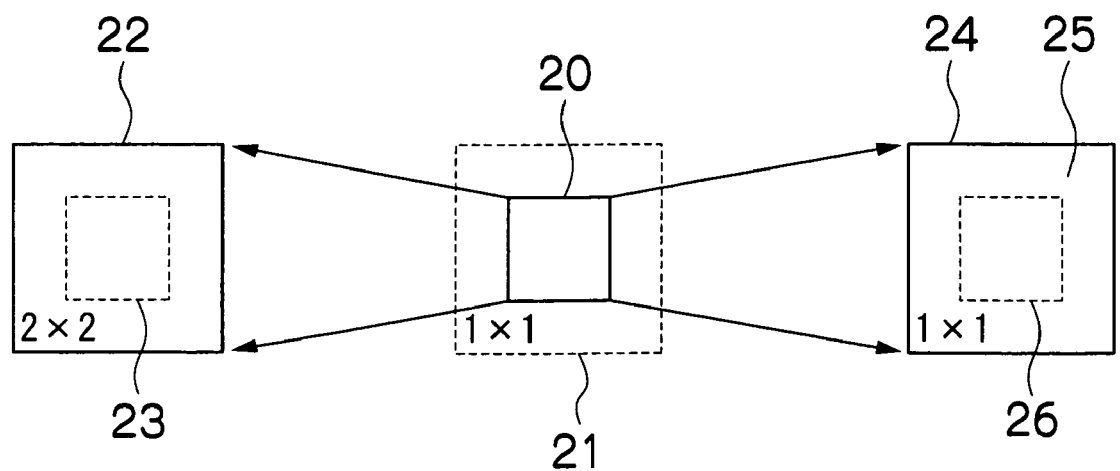
FIG. 5 is a diagram used to describe a method of calculating offset data in the entire region fluoroscopy mode and the radiography mode from the offset data acquired in the partial region fluoroscopy mode.

FIG. 5 shows an effective area, a pixel size and so on of the X-ray flat panel detector in each of the entire region fluoroscopy mode, the partial region fluoroscopy mode and the radiography mode.

In FIG. 5, reference numeral 20 denotes the effective area in the partial region fluoroscopy mode of the entire area 21 of the X-ray flat panel detector, where an element (1×1) of the X-ray flat panel detector in the area 20 corresponds to a pixel of a partial region fluoroscopy image.

Reference numeral 22 denotes the effective area in the entire region fluoroscopy mode, where the four elements (2×2) of the X-ray flat panel detector in the area 22 is corresponding to a pixel of the entire region fluoroscopy image. Reference numeral 23 denotes the area corresponding to the effective area 20 in the partial region fluoroscopy mode.

Reference numeral 24 denotes the effective area in the radiography mode, where an element (1×1) of the X-ray flat panel detector in the area 24 corresponds to a pixel of the shot image. Reference numeral 25 denotes the area corresponding to the effective area 20 in the partial region fluoroscopy mode.

If the offset data in the area 20 is newly calculated in the partial region fluoroscopy mode, the offset data in the entire region fluoroscopy mode and the radiography mode can be calculated as follows.

(Offset data in the entire region fluoroscopy mode)

(1) The offset data of all the pixels in the area 22 stored in the offset data storage means 7 is converted and updated based on an average coefficient of fluctuation of the newly calculated offset data in the area 20 (that is, the area 23).

(2) The newly calculated offset data in the area 20 is used to calculate the offset data in the area 23 corresponding to the area 20 by the formula (1), and the offset data in other areas is calculated by using the average coefficient of fluctuation of the offset data in the area 20 as in (1). The method of (2) has better precision of the offset data in the area 23 compared to the method of (1).

(Offset data in the radiography mode)

(3) The offset data of all the pixels in the area 24 stored in the offset data storage means 7 is converted and updated based on the average coefficient of fluctuation of the newly calculated offset data in the area 20 (that is, the area 26).

(4) As for the offset data in the area 26, the newly calculated offset data in the area 20 is adopted as-is, and the other offset data in the area 25 is calculated by using the average coefficient of fluctuation of the offset data in the area 26 as in (3). The method of (4) has better precision of the offset data in the area 26 compared to the method of (3), and it is especially effective in the area 26 because there are many cases where it is at the center of the X-ray flat panel detector and has an important portion for diagnosis represented therein.

In the above embodiment, the case of setting and updating the offset data for each pixel of the image in each mode has been described. However, it is not limited thereto and the present invention is also applicable to the case of setting and updating the offset data for each readout channel of the X-ray flat panel detector in each mode. The plurality of modes are not limited to those described above. And the type of the X-ray flat panel detector may be either a direct type or an indirect type.

INDUSTRIAL APPLICABILITY

As described above, the X-ray diagnosis apparatus according to the present invention uses the offset data acquired in one of the plurality of modes of which number of pixels and number of elements constituting one pixel are different to calculate the offset data in another mode. Therefore, it can update the offset data in all the modes by acquiring the offset data once. Thus, it can perform a precise offset correction equivalent to acquiring current offset data in all the modes. And upon switching from one mode (first mode) to another mode (second mode), it can immediately eliminate an artifact from the image in the second mode so as to obtain an optimum image for diagnosis.

The invention claimed is:

1. An X-ray diagnosis apparatus comprising:
   an X-ray generator for generating an X-ray according to an X-ray generating condition of an image acquisition mode selected from a plurality of image acquisition modes;
   an X-ray detector for receiving incidence of the X-ray generated by the X-ray generator, the X-ray detector converts the incident X-ray to an image signal and processes the image signal according to a signal processing condition of the selected image acquisition mode to thereby output image data in the selected image acquisition mode;
   storage means for storing each of offset data in the plurality of image acquisition modes;
   first mode offset data calculation means for, when a first mode of the plurality of image acquisition modes is selected, calculating new offset data in the first mode based on offset image data outputted from the X-ray detector in a state that the X-ray is not incident on the X-ray detector and first mode offset data stored in the storage means;
   second mode offset data calculation means for calculating new offset data in a second mode based on second mode offset data of the plurality of image acquisition modes stored in the storage means and the new offset data in the first mode;
   image calculation means for, when the second mode is selected, calculating a second mode X-ray image from the image data outputted from the X-ray detector in a state that the X-ray is incident on the X-ray detector and the new offset data in the second mode; and
   display means for displaying the X-ray image.

2. The X-ray diagnosis apparatus according to claim 1, wherein the offset data stored in the storage means is acquired in advance in the state that the X-ray is not incident on the X-ray detector.

3. The X-ray diagnosis apparatus according to claim 1, wherein the second mode offset data calculation means calculates the new offset data in the second mode by converting the second mode offset data stored in the storage means based on at least one of an update amount and an update rate of the new offset data in the first mode.

4. The X-ray diagnosis apparatus according to claim 1, wherein the first mode offset data calculation means calculates the offset data in the first mode by obtaining arithmetic means of a plurality of the offset image data in the first mode for each pixel of the offset image data.

5. The X-ray diagnosis apparatus according to claim 1, wherein the first mode offset data calculation means takes the arithmetic mean of a plurality of the offset image data in the first mode for each readout channel of the X-ray detector so as to calculate the offset data in the first mode.

6. The X-ray diagnosis apparatus according to claim 1, wherein the image calculation means calculates the X-ray image by subtracting offset data from the image data.

7. The X-ray diagnosis apparatus according to claim 1, further comprising input means for inputting an instruction to update offset data, and when the instruction is inputted, the first mode offset data calculation means sets the state that the X-ray is not incident on the X-ray detector so as to newly calculate the offset data.

8. The X-ray diagnosis apparatus according to claim 1, wherein the first and the second modes are a different two of an entire region fluoroscopy mode, a partial region fluoroscopy mode and an radiography mode.

9. The X-ray diagnosis apparatus according to claim 1, wherein the X-ray detector is an X-ray flat panel detector.

* * * * *